United States Patent
Sebok et al.

[11] Patent Number: 6,104,483
[45] Date of Patent: Aug. 15, 2000

[54] OPTICAL FLOW CELL WITH REFERENCES FLANGE

[75] Inventors: Thomas J. Sebok, Tallmadge; John F. Brewer, Mogadore; Steve G. Fockler, North Canton; Craig J. Holloway, Stow, all of Ohio

[73] Assignee: Lockheed Martin Tactical Defense Systems, Inc., Akron, Ohio

[21] Appl. No.: 09/336,398

[22] Filed: Jun. 18, 1999

[51] Int. Cl.[7] ............................................. G01N 21/01
[52] U.S. Cl. .............................................................. 356/244
[58] Field of Search ................................. 356/246, 244, 356/440; 250/573, 574

[56] References Cited

U.S. PATENT DOCUMENTS

| | | | |
|---|---|---|---|
| 3,198,064 | 8/1965 | Moore | 88/14 |
| 3,947,121 | 3/1976 | Cotter et al. | 356/38 |
| 4,393,466 | 7/1983 | Deindoerfer et al. | 364/415 |
| 4,582,684 | 4/1986 | Vogel et al. | 422/57 |
| 4,804,267 | 2/1989 | Greenfield | 356/335 |
| 4,807,267 | 2/1989 | Rifu et al. | 378/7 |
| 5,030,421 | 7/1991 | Muller | 422/102 |
| 5,098,661 | 3/1992 | Froehlich et al. | 422/102 |
| 5,241,189 | 8/1993 | Vandagriff et al. | 250/575 |
| 5,594,544 | 1/1997 | Horiuchi et al. | 356/73 |
| 5,766,957 | 6/1998 | Robinson et al. | 436/165 |
| 5,883,721 | 3/1999 | Gilby et al. | 356/440 |

FOREIGN PATENT DOCUMENTS

WO 95/12118  5/1995  WIPO .

*Primary Examiner*—Frank G. Font
*Assistant Examiner*—Philip Natividad
*Attorney, Agent, or Firm*—Renner, Kenner, Greive, Bobak, Taylor & Weber

[57] ABSTRACT

An optical flow cell includes a housing having an inlet coupled to an outlet through which a sample fluid material flows. A viewing assembly, carried by the housing, includes a pair of opposed plates having a gap therebetween which is in fluid communication between the inlet and the outlet. One of the plates extends outwardly from the housing for use as a reference point in a fluid sampling device. The flow cell is positioned between a light source and an imaging system to detect particle shape and size as the fluid passes through the viewing assembly.

23 Claims, 2 Drawing Sheets

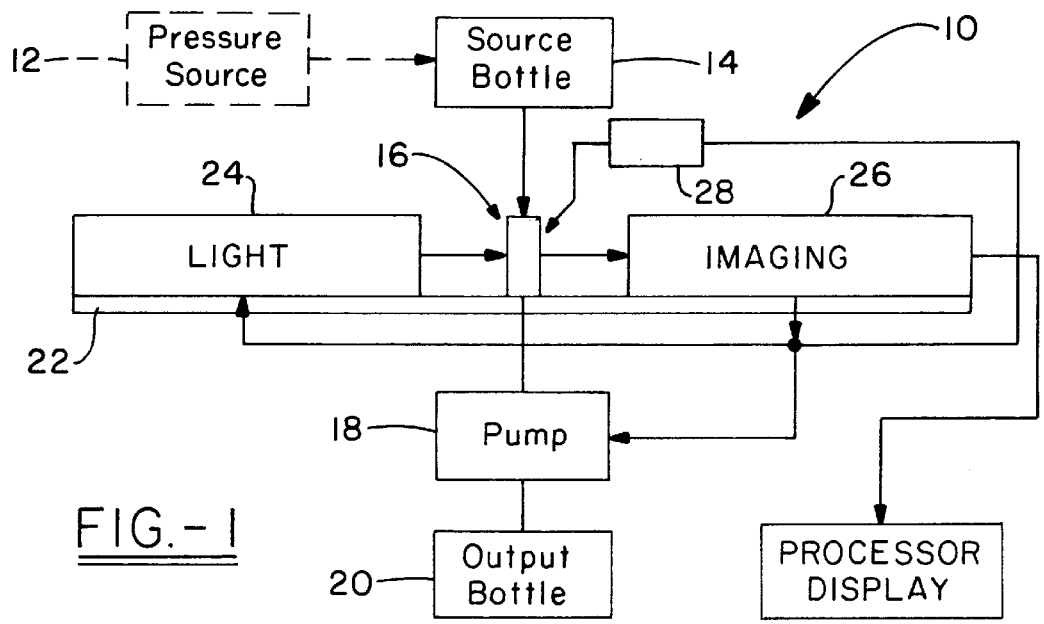
FIG.-1
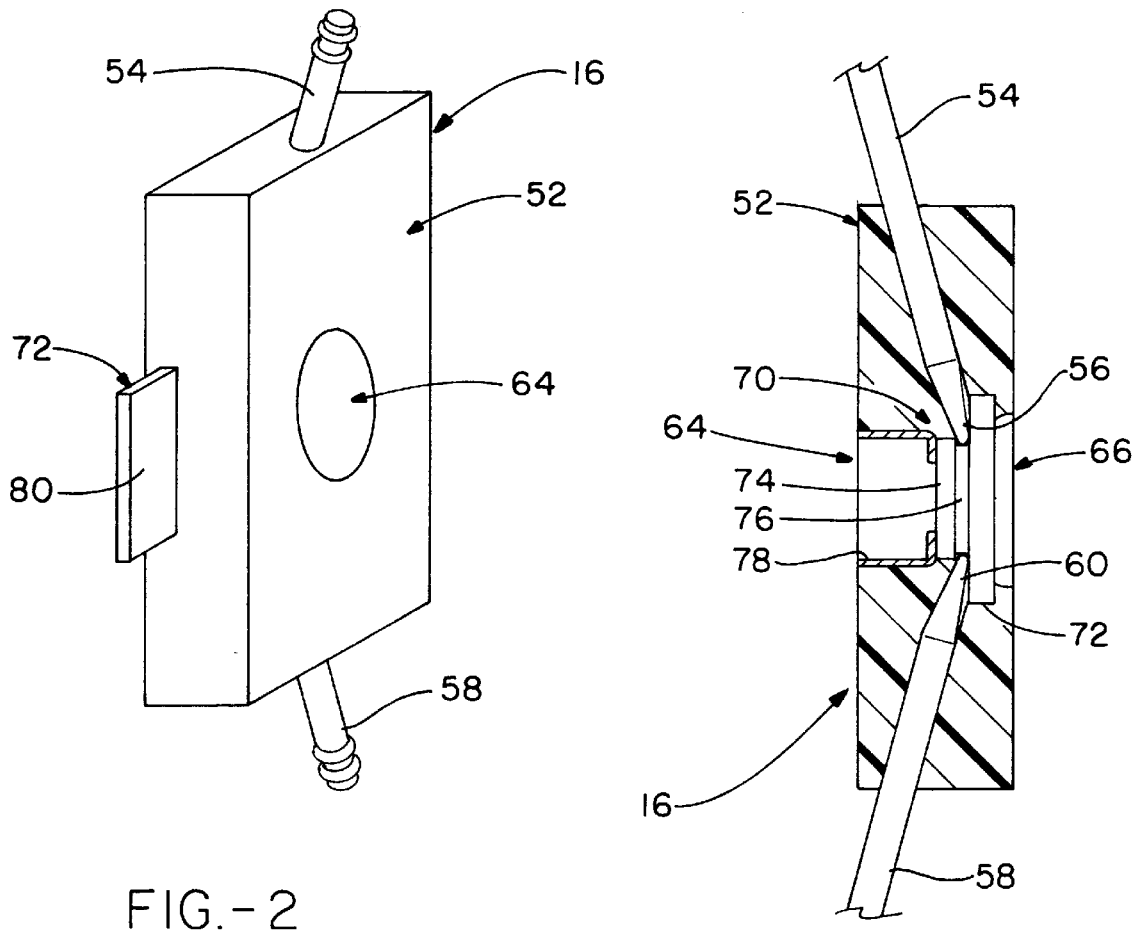
FIG.-2
FIG.-3

OPTICAL FLOW CELL WITH REFERENCES FLANGE

TECHNICAL FIELD

The present invention relates generally to fluid inspection systems. More particularly, the invention relates to an optical flow cell through which the fluid under inspection passes. Specifically, the invention relates an optical flow cell which provides an accurate reference point for repeatable analysis of the fluid by an imaging system contained in the fluid inspection system.

BACKGROUND ART

It is known to provide fluid sampling devices using optical near-field imaging as disclosed in U.S. Pat. No. 5,572,320, which is incorporated herein by reference. Such a device is employed to determine quantity, size, characteristics, and types of particulate matter in fluids. Examples of fluids which are monitored in such a system are lubricating oils used in engines and rotating machinery; and fluids used in industrial quality control, food processing, medical analysis, and environment control. In its most common use, such a device monitors engine oil for metal particulates or flakes, wherein a size, number, and shape of particulates correspond to an engine condition and can alert one to particular problems with the engine. Predicting failure is critically important in aircraft engines to avoid accidents and loss of life.

The early stages of engine wear cause small particulate matter, of about 50 microns or less in size, to be generated. These particulates have characteristic shapes indicative of the type of wear produced by specific wear mechanisms. As the wear process progresses, the amount and size of particulates increase. Accordingly, sensing and identifying smaller particles allows early identification of faults, thus, allowing more time for corrective maintenance and preventing unexpected catastrophic failures.

Although current devices are sufficient in their stated purpose, several problems have materialized. For example, the flow pattern, which is analyzed through an optical flow cell carried by the sampling device, is not uniform. As such, non-uniform flow biases the particle distribution and may result in the inability to properly monitor the fluid and, in some cases, generate false positives. In other words, an inaccurate particle distribution may indicate that a problem exists with the engine when, in fact, there is not. Due to the small particle size and the positioning of the flow cell, the gap between the viewing plates and their positioning is of utmost importance. Current systems do not provide a repeatable frame of reference to provide adequate evaluation of the fluid as it flows through the optical flow cell. This is evident when the optical flow cells are damaged and must be replaced.

As will be appreciated by the discussion above, obtaining a uniform and consistent cell gap thickness, a positioning reference and a means of transitioning the fluid from a tube to the cell gap while maintaining a uniform flow is critical in obtaining consistent results over the life of the sampling device. Existing flow cells do not perform all of these functions, can be costly to manufacture, and can be prone to leakage. The molded device described here has the potential for being manufactured cheaply. Therefore, there is a need in the art for low cost replaceable optical flow cells which require minimal calibration and which maintain their characteristics for a long period of time.

SUMMARY OF THE INVENTION

It is thus an object of the present invention to provide a fluid inspection system to evaluate and analyze fluids which contain particulate material.

It is another object of the present invention to provide an inspection system, as set forth above, that includes a light source which projects light, such as laser light, through a fluid specimen so as to generate an image captured by an imaging system which analyzes the shape and number of particulates in the fluid. The light source may be projected through the specimen to impinge upon the imaging system. Alternatively, or in addition to the projecting light source, a frontal light source may illuminate the other side of the fluid specimen to provide color information of the specimen or the like.

It is yet another object of the present invention to provide a fluid inspection system, as set forth above, that includes an optical flow cell housing disposed between the light source and the imaging system, wherein the housing includes a tapered inlet and a tapered outlet to provide a uniform flow of the fluid into a viewing area of the flow cell.

It is still another object of the present invention to provide a fluid inspection system, as set forth above, wherein the viewing area is defined by opposed plates contained within the cell housing.

It is a further object of the present invention to provide a fluid inspection system, as set forth above, wherein one of the plates extends outwardly from the housing to provide a reference point for the imaging system.

Yet a further object of the present invention is to provide a fluid inspection system, as set forth above, wherein the housing is detachably mounted to a bracket assembly provided by the inspection system.

It is still a further object of the present invention to provide a fluid inspection system, as set forth above, in which the housing provides a light entry aperture and an imaging aperture adjacent respective opposed plates within the housing.

It is an additional object of the present invention to provide a fluid inspection system, as set forth above, wherein a mask is applied to the light entry aperture so as to further enhance the imaging of the particles flowing through the optical flow cell by reducing the light scattering path around the fluid sample and through the flow cell body.

The foregoing and other objects of the present invention, which shall become apparent as the detailed description proceeds, are achieved by an optical flow cell, comprising a housing having an inlet coupled to an outlet through which a fluid material flows and a viewing assembly comprising a pair of opposed optical plates having a gap therebetween which is in fluid communication between the inlet and the outlet, the viewing assembly carried by the housing, wherein one of the plates extends outwardly from the housing for use as a reference point.

Other aspects of the present invention are attained by a fluid sampling device, comprising at least one light source, an imaging system operatively positioned with respect to the light source, an optical flow cell positioned between the light source and the imaging system, the optical flow cell having an outwardly extending flange, and a cell bracket for mounting the optical flow cell by the outwardly extending flange at a predetermined position from the imaging system.

Still other aspects of the present invention are attained by a method for constructing an optical flow cell, comprising the steps of providing a reference plate, disposing substantially parallel bonding strips on said reference plate, positioning a sealing plate on said bonding strips so as to form a fluid gap, curing said bonding strips so as to secure said reference plate to said sealing plate, and molding a material about said plates while forming an inlet and an outlet to allow fluid communication through said gap, and form the optical flow cell.

These and other objects of the present invention, as well as the advantages thereof over existing prior art forms, which will become apparent from the description to follow, are accomplished by the improvements hereinafter described and claimed.

BRIEF DESCRIPTION OF THE DRAWINGS

For a complete understanding of the objects, techniques and structure of the invention, reference should be made to the following detailed description and accompanying drawings, wherein:

FIG. 1 is schematic diagram of a fluid inspection system according to the present invention;

FIG. 2 is a perspective drawing of an improved optical flow cell according to the present invention;

FIG. 3 is a cross-sectional view of the optical flow cell according to the present invention;

BEST MODE FOR CARRYING OUT THE INVENTION

Figure 4:
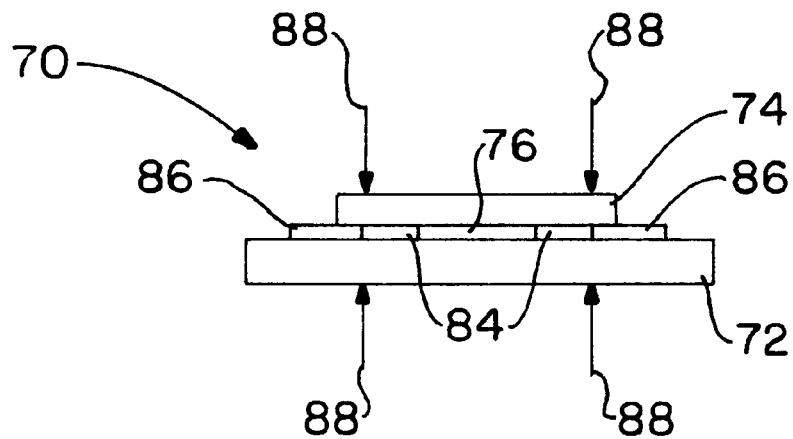
FIG. 4 is an elevational view of a viewing assembly enclosed within the optical flow cell.
Figure 5:
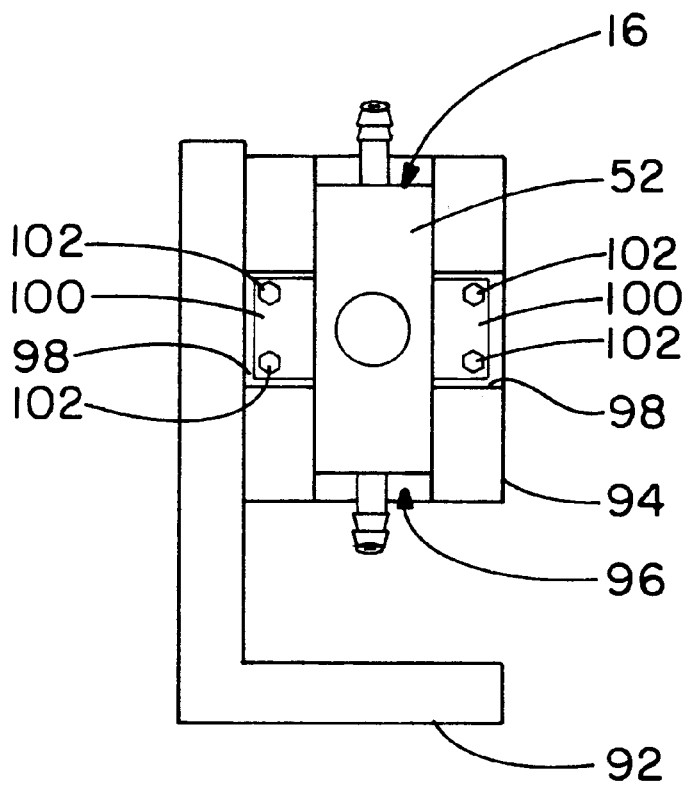
FIG. 5 is an end view of a cell bracket assembly for carrying the optical flow cell.

Referring now to the drawings and more particularly to FIG. 1, it can be seen that a fluid sample inspection system, according to the present invention, is designated generally by the numeral 10. As is known in the art, a pressure source 12 may be coupled to a bottle or container 14 of sample material fluid. It is envisioned that the sample bottle 14 will carry oil that is used to lubricate machine parts, such as engines, transmissions, and the like. The system 10 could also be employed to analyze any type of fluid which contains particles that need to be evaluated. Application of the pressure source 12 to the sample bottle of fluid 14 causes the material or fluid contained within the bottle to migrate or flow through an optical flow cell 16 for analysis. Coupled to the opposite side of the flow cell 16 may be a pump 18 which pulls or draws the material through the cell. Those skilled in the art will appreciate that the pressure source 12 and the pump 18 may be employed in conjunction with one another or may be operated separately to draw the sample fluid material through the cell 16. The sample fluid material is then deposited into an output bottle 20 for storage and/or further analysis.

A plate 22 supports and carries the optical flow cell 16. Also supported by the plate 22 is a light source 24, which in the preferred embodiment, employs a laser diode with associated collimating optics to direct light through one side of the flow cell 16 and the sample fluid material. This generates an image or shadow received and detected by an imaging system 26 that is also supported by the plate 22. The imaging system 26 is coupled to a processor-based display system (not shown) for classifying the particles, for determining the number of particles contained within the sample, and for analyzing other features of the fluid.

An alternative light source 28, which may be used in conjunction with, or in alternative to the light source 24, is positioned on an opposite side of the optical flow cell 16. The light source 28 may project a white light to facilitate the detection of the particle's color for further classification or analysis.

Referring now to FIGS. 2 and 3, it can be seen that the optical flow cell 16, according to the present invention, includes a housing 52 which is preferably of a molded construction, using a material such as epoxy. In the preferred embodiment, the epoxy is Ciba-Geigy Araldite GY502 modified epoxy resin cured with triethylenetetramine (TETA). The housing 52 includes an inlet 54 which is coupled to the sample bottle of fluid 14 and wherein the inlet 54 has a tapered end 56. The housing 52 also includes an outlet 58 which has a tapered end 60. One side of the housing 52 provides a light entry aperture 64 which is positioned proximal the light source 24. The opposite side of the housing 52 provides an imaging aperture 66 which is proximally positioned adjacent to the imaging system 26.

A viewing assembly 70 is incorporated into the housing 52 and is positioned between the light entry aperture 64 and the imaging aperture 66. The viewing assembly 70 includes a reference plate 72 which is opposed by a sealing plate 74. Each plate 72 and 74 has a precisely controlled thickness to provide for a repeatable focal distance. In the preferred embodiment, each plate is flat on both sides and is optically clear and defect free. The plates 72 and 74 are positioned and constructed so as to form a fluid gap 76 therebetween, which is in fluid communication with the tapered ends 56 and 60. A mask 78 may be disposed upon selected portions of the light entry aperture 64 so as to direct the light through the viewing assembly 70 in the desired area and to enhance the contrast and imaging of the sample fluid material 14. A flange 80 extends from each side of the housing 52, wherein the flange 80 is an integral extension of the reference plate 72.

Construction of the viewing assembly 70 is best seen in FIG. 4. The plates 72 and 74 are typically glass plates with excellent optical properties. The reference plate 72, which is the longer of the two plates, has a closely controlled thickness for a repeatable focal distance, is placed upon a clean base surface. A fiberglass cloth impregnated with an epoxy resin ("prepreg") is placed on the reference plate in two spaced-apart, substantially parallel bonding strips 84. The area between the parallel bonding strips 84 forms the gap 76 when the viewing assembly is completed. A pair of shims 86, which are about 100 microns in thickness, are placed adjacent to and in parallel with the outer edges of the bonding strips 84. The reference plate 74 is then disposed over the bonding strips 84 and the shims 86, whereupon a clamping force 88 is applied to both the plates. Once the prepreg material is cured, the shims 86 are removed and the viewing assembly 70 is then placed into a mold such that the reference plate extends outwardly from both side edges of the mold. The mold seals around the reference plate 72 to form the extending flanges 80. The inlet 54 and the outlet 58 are angularly positioned in the mold such that the respective tapered openings of the inlet and outlet are in fluid communication with each end of the gap 70. The tapered inlets provide a transition from a circular cross-section into a rectangular cross-section so that along with the reference plate and sealing plate, a substantially rectangular entry and exit portion for the gap 72 is formed. As will be appreciated by those skilled in the art, this provides a smooth and uniform transition from the sample bottle 14 into the viewing area of the flow cell 16. The transition from the circular to rectangular cross-section may be formed by an appropriately shaped insert positioned into the inlet and outlet, and the gap 76 prior to molding. Once the assembly is loaded into the mold, all crevices between the mold and viewing assembly 70 are sealed with a filled epoxy. The filled epoxy is Ciba-Geigy Araldite GY502 modified epoxy resin, Fisher Scientific triethylenetetramine, and Cabot Corporation Cab-O-Sil M5 filmed silica mixed in the ratio of 10:1:0.7 to yield a thick paste. The epoxy sealant is allowed to gel. Next, an epoxy is mixed in a 10 to 1 ratio as above, but without the Cab-O-Sil material, and poured into the mold. The viewing apertures 64 and 66 are formed by plungers or other inserts positioned on the respective plates prior to pouring of the epoxy into the mold. The assembly is then allowed to set overnight, or for at least 16 hours, at room temperature. Then the part is removed from the mold, whereupon flash and extraneous epoxy are trimmed from the part. The part is cleaned and sanded to present the optical flow cell 16. An epoxy mask 78 is applied around the light entry aperture to form a viewing window which allows entry of light into the viewing assembly 70.

Upon completion of the construction of the flow cell 16, it is placed within the inspection system 10. The inspection system 10 includes a horizontally positioned plate 92 which has an upwardly extending cell bracket 94. The cell bracket 94 provides a substantially vertical channel 96 for receiving the housing 52. A pair of perpendicularly extending grooves 98 extend from the channel 96 for receiving the flanges 80 of the housing 52. Once the housing 52 is set into position, a pair of clamp plates 100 are secured over the flanges 80 by fasteners 102. Connecting tubes are then coupled between the sample bottle 14 and the inlet 58 and between the outlet 58 and the collection bottle 20.

With the mask 78 in place, a viewing area of about 1600 microns by 1200 microns is provided on the sealing plate 72. In view of the shims used in the construction of the viewing assembly 70, a gap of about 100 microns is obtained. Of course, this size can be adjusted depending upon the material being analyzed.

It is apparent from the above description of the construction and use of the optical flow cell 16, that the problems associated with current inspection systems have been overcome. In particular, by employing a reference plate 72 that extends beyond the edges of the housing 52, a reference plate is easily used as a position reference point to place the flow cell 16 in a predetermined location from the imaging system 16. It will be appreciated by those skilled in the art of the critical importance of placement of the viewing assembly in the field of view of the imaging system due to the typical small particle size that must be monitored. Yet another advantage of the present invention is the angular and tapered flow from the inlet 54 to the tapered end 56 into the gap 70 and the corresponding flow outwardly from the gap 76 into the tapered end 60 to the outlet 58. It will be appreciated that such a construction allows for reversal of the inlet 54 and outlet 58 without adversely affecting the performance of the inspection system 10. Still yet another advantage of the present invention is the employment of a mask 78 about the light entry aperture 64 so as to enhance the viewing and imaging of any particles flowing through the gap 76 by reducing the light scattered around the flow cell. This allows for proper image generation of the imaging system 26. By employing the flanges 80 as the reference point of the reference plate 72, recalibration of the inspection system is significantly reduced and allows for repeatability between analysis of various types of samples when a flow cell is replaced.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of true scope and breadth of the invention, reference should be made to the following claims.

What is claimed is:

1. An optical flow cell, comprising:
    a housing having an inlet coupled to an outlet through which a fluid material flows; and
    a viewing assembly comprising a pair of opposed plates having a gap therebetween which is in fluid communication between said inlet and said outlet, said viewing assembly carried by said housing, wherein one of said plates rigidly extends outwardly from both sides of said housing to form a flange for use as a reference point so that the fluid material flowing through the gap is in an object plane.

2. An optical flow cell, comprising:
    a housing having an inlet coupled to an outlet through which a fluid material flows; and
    a viewing assembly comprising a pair of opposed plates having a gap therebetween which is in fluid communication between said inlet and said outlet, said viewing assembly carried by said housing, wherein one of said plates extends outwardly from said housing for use as mechanical mounting points while providing a repeatable reference point along an axis substantially perpendicular to the plates, wherein said housing includes a recessed light entry aperture opposite a recessed imaging aperture, wherein one of said plates is exposed to said light entry aperture and the other of said plates is exposed to said recessed imaging aperture.

3. The optical flow cell according to claim 2, further comprising a mask selectively disposed on said light entry aperture.

4. An optical flow cell, comprising:
    a housing having an inlet coupled to an outlet through which a fluid material flows; and
    a viewing assembly comprising a pair of opposed plates having a gap therebetween which is in fluid communication between said inlet and said outlet, said viewing assembly carried by said housing, wherein one of said plates extends outwardly from said housing for use as mechanical mounting points while providing a repeatable reference point along the axis substantially perpendicular to the plates, wherein said inlet transitions from a circular cross-section to a rectangular cross-section which is in fluid communication with said gap.

5. The optical flow cell according to claim 4, wherein said outlet transitions from a rectangular cross-section which is in fluid communication with said gap to a circular cross-section.

6. A fluid sampling device, comprising:
    at least one light source;
    an imaging system operatively positioned with respect to said light source;
    an optical flow cell positioned between said light source and said imaging system, said optical flow cell having a rigid outwardly extending flange, said optical flow cell comprising
        a housing having an inlet coupled to an outlet through which the fluid sample flows; and
        a pair of opposed plates having a gap therebetween which is in fluid communication with said inlet and said outlet, one of said opposed plates providing said rigid outwardly extending flange that extends from both sides of the other said opposed plate;
    means for directing a fluid sample through said optical flow cell for observation said imaging system; and
    a cell bracket for mounting said optical flow cell by said outwardly extending flange at a predetermined position from said imaging system.

7. The fluid sampling device according to claim 6, wherein said cell bracket further includes a channel for receiving said optical flow cell and an angularly extending groove for receiving said flange.

8. The fluid sampling device according to claim 7, further comprising at least one clamp plate for fastenably securing said flange in said groove.

9. The fluid sampling device according to claim 6, wherein said housing includes a recessed light entry aperture positioned proximal said light source.

10. The fluid sampling device according to claim 9, further comprising a mask selectively disposed on said light entry aperture.

11. The fluid sampling device according to claim 9, wherein said housing includes a recessed imaging aperture positioned proximal said imaging system.

12. The fluid sampling device according to claim 11, wherein said recessed imaging apparatus is at least partially formed by said plate providing said outwardly extending flange.

13. The fluid sampling device according to claim 6, wherein said means for directing comprises a pump.

14. The fluid sampling device according to claim 6, wherein said means for directing comprises a pressure source.

15. The fluid sampling device according to claim 14, wherein said means for directing further comprises a pump.

16. The fluid sampling device according to claim 6, wherein said at least one light source is positioned on the opposite side of said optical flow cell as said imaging system.

17. The fluid sampling device according to claim 16, further comprising another light source positioned on a same side of said optical flow cell.

18. The fluid sampling device according to claim 6, wherein said at least one light source is positioned on the same side of said optical flow cell as said imaging system.

19. A method for constructing an optical flow cell, comprising the steps of:

providing a reference plate;

disposing substantially parallel bonding strips on said reference plate;

positioning a sealing plate on said bonding strips so as to form a fluid gap;

curing said bonding strips so as to secure said reference plate to said sealing plate;

angularly positioning an inlet tube and an outlet tube at ends of said fluid gap; and molding a material about said plates while forming an inlet and an outlet to allow fluid communication through said gap, and form the optical flow cell, said inlet and outlet tubes providing a rectangular to a circular cross-sectional transition away from said gap.

20. A method for constructing an optical flow cell, comprising the steps of:

providing a reference plate;

disposing substantially parallel bonding strips on said reference plate;

positioning a sealing plate on said bonding strips so as to form a fluid gap;

curing said bonding strips so as to secure said reference plate to said sealing plate; and molding a material about said plates while forming an inlet and an outlet to allow fluid communication through said gap, and form the optical flow cell;

positioning a plunger on each said plate prior to said molding step to form a light entry aperture adjacent said sealing plate and an imaging aperture adjacent said reference plate.

21. The method according to claim 20, further comprising the step of:

applying a mask around said light entry aperture to form a viewing window.

22. The method according to claim 19, further comprising the step of:

disposing a shim of predetermined thickness between said plates prior to said positioning step;

clamping said plates during curing of said bonding strips; and removing said shim after curing of said bonding strips.

23. The method according to claim 19, further comprising the step of:

positioning said bonded reference plate and sealing plate in a mold so that said reference plate extends from said material for use as a reference point.

* * * * *